(12) United States Patent
Hoenes et al.

(10) Patent No.: US 9,138,179 B2
(45) Date of Patent: Sep. 22, 2015

(54) FLEXIBLE LANCET

(75) Inventors: Joachim Hoenes, Zwingenberg (DE); Uwe Kraemer, Ilvesheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1373 days.

(21) Appl. No.: 12/129,065

(22) Filed: May 29, 2008

(65) Prior Publication Data

US 2008/0300509 A1 Dec. 4, 2008

(30) Foreign Application Priority Data

May 29, 2007 (EP) .................................... 07010561

(51) Int. Cl.
*A61B 5/00* (2006.01)
*B65D 81/00* (2006.01)
*A61B 17/14* (2006.01)
*A61B 17/32* (2006.01)
*A61B 5/15* (2006.01)
*A61B 5/145* (2006.01)
*A61B 5/151* (2006.01)

(52) U.S. Cl.
CPC ........... *A61B 5/1411* (2013.01); *A61B 5/15146* (2013.01); *A61B 5/14532* (2013.01); *A61B 5/151* (2013.01); *A61B 5/15142* (2013.01); *A61B 5/15186* (2013.01)

(58) Field of Classification Search
CPC .. A61B 5/1411; A61B 5/14532; A61B 5/151; A61B 5/15142; A61B 5/15146; A61B 5/15186
USPC ........... 600/573, 576–584; 606/167, 181–183
See application file for complete search history.

(56) References Cited

U.S. PATENT DOCUMENTS

| | | | |
|---|---|---|---|
| 3,802,842 A | 4/1974 | Lange et al. | |
| 4,061,468 A | 12/1977 | Lange et al. | |
| 4,414,975 A | 11/1983 | Ryder et al. | |
| 4,490,465 A | 12/1984 | Limbach et al. | |
| 4,924,879 A | 5/1990 | O'Brien | |
| 5,173,261 A | 12/1992 | Krause et al. | |
| 5,284,622 A | 2/1994 | Krause et al. | |
| 5,318,584 A | 6/1994 | Lange et al. | |
| 5,630,828 A | 5/1997 | Mawhirt et al. | |
| 6,210,421 B1 | 4/2001 | Bocker et al. | |
| 6,616,616 B2 * | 9/2003 | Fritz et al. | 600/583 |
| 7,004,928 B2 * | 2/2006 | Aceti et al. | 604/191 |

(Continued)

FOREIGN PATENT DOCUMENTS

DE 3217757 12/1982
DE 196 04 156 A1 8/1997

(Continued)

*Primary Examiner* — Devin Henson
(74) *Attorney, Agent, or Firm* — Bose McKinney & Evans LLP

(57) ABSTRACT

A system for withdrawing body fluid is described which has a housing with at least one opening and at least one lancet which is elongate and substantially straight in its original and unused form. The lancet has a distal end with a lancet tip for carrying out a lancing operation. The system also includes a drive unit for driving the lancet in a drive direction and at least one guide element which makes contact with the lancet at least during the lancing operation and guides the lancet movement such that the lancet is bent relative to the drive direction. The lancet can have a high restoring force such that it returns to its original substantially straight shape after contacting the guide element.

56 Claims, 3 Drawing Sheets

(56) References Cited

U.S. PATENT DOCUMENTS

| | | |
|---|---|---|
| 7,223,248 B2 * | 5/2007 | Erickson et al. ............... 600/584 |
| 7,343,188 B2 * | 3/2008 | Sohrab ........................... 600/345 |
| 7,481,777 B2 * | 1/2009 | Chan et al. ..................... 600/583 |
| 7,909,776 B2 * | 3/2011 | Roe et al. ....................... 600/583 |
| 7,959,581 B2 * | 6/2011 | Calasso et al. ................ 600/583 |
| 7,985,203 B2 * | 7/2011 | Haueter et al. ................ 604/158 |
| 2002/0052618 A1 | 5/2002 | Haar et al. |
| 2002/0123740 A1 * | 9/2002 | Flaherty et al. ............. 604/890.1 |
| 2003/0199902 A1 | 10/2003 | Boecker et al. |
| 2004/0193202 A1 | 9/2004 | Allen |
| 2005/0245845 A1 | 11/2005 | Roe et al. |
| 2006/0142698 A1 * | 6/2006 | Ethelfeld ....................... 604/157 |
| 2006/0264996 A1 * | 11/2006 | LeVaughn et al. ............ 606/181 |

FOREIGN PATENT DOCUMENTS

| | | |
|---|---|---|
| EP | 0 477 322 | 10/1991 |
| EP | 0 535 480 A1 | 9/1992 |
| EP | 0 565 970 A1 | 4/1993 |
| EP | 0 885 591 A2 | 12/1998 |
| EP | 1 203 563 A2 | 10/2001 |
| EP | 1 360 935 A1 | 11/2003 |
| WO | WO 91/16626 A1 | 10/1991 |
| WO | WO 2005/117721 | 12/2005 |

* cited by examiner

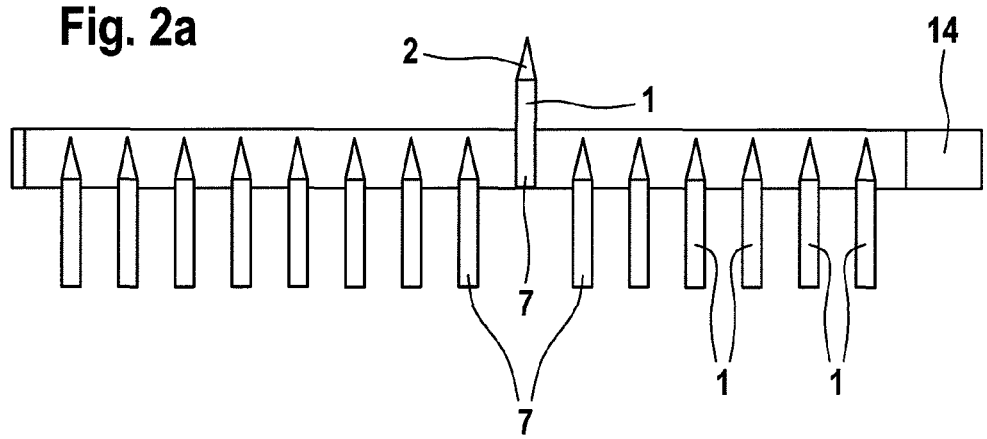
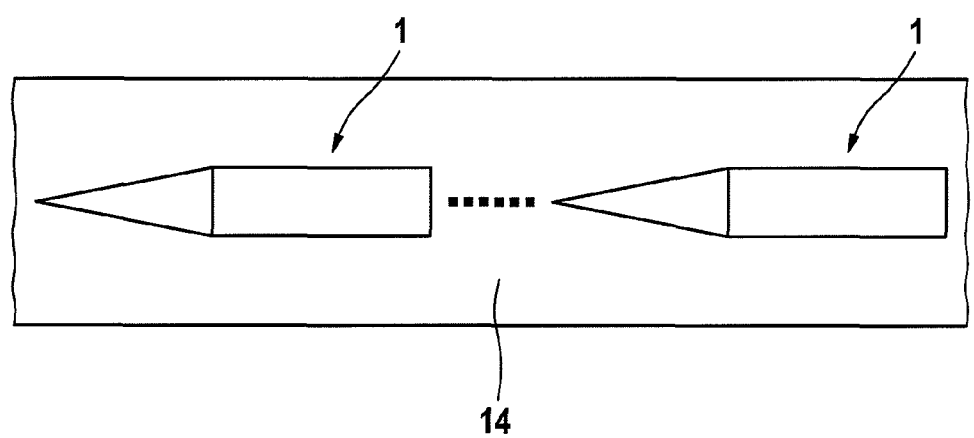

FLEXIBLE LANCET

RELATED APPLICATIONS

This application claims priority to EP 07 010 561.4, filed May 29, 2007, which is hereby incorporated by reference in its entirety.

BACKGROUND

The present invention relates to lancing aids for the diagnostic determination of blood parameters. Body fluids are collected and analyzed in many fields of medical diagnostics, and it is therefore desirable to enable routine tests to be carried out outside the laboratory in a rapid and reproducible manner. The testing can be carried out with various body fluids such as, e.g., blood and/or interstitial fluid. These fluids can be examined for various characteristics. The results of this examination are important in order to be able to make reliable diagnoses, to carry out therapeutic measures and for therapeutic monitoring.

The analysis of body fluids starts with collection of the fluid. One method for obtaining body fluid is to generate a very small wound in the skin of the patient with the aid of a needle, lancet or a knife. The body fluid obtained in this manner can then either be collected in small vessels or it can be directly brought into contact with a test element such as a test strip for analysis. In order to avoid injury to the patient when using lancets, needles or blades, the lancing aid is typically constructed with a protector or cover on the lancing tip. Most of these lancing aids require manual insertion of the lancet into the lancing aid. This is a laborious operation when the lancing aid is used frequently. Storage of lancets in a magazine can obviate this problem, but many safety aspects have to be followed. Thus, for example, the safety of the patient during use of the lancing aid must be ensured. Furthermore, the system should not be too complex because otherwise it could not be easily handled by the patient.

A few solutions for this are disclosed in the prior art. U.S. Publication No. 2003/0199902 ensures a sealing of each individual lancet in a magazine in which a complicated and space-filling gear wheel mechanism is used to transport the lancets out of the magazine.

An analytical device is described in the EP 1 203 563. This device has a test element on a carrier tape and an additional frame element is mounted on this test element which is movable and comprises a lancet. During use, the frame element can be moved from a parallel position relative to the test element into an orthogonal position so that the lancet can be actuated through an opening in the test element. This is a quite complicated implementation of a combination of test element and lancet because many parts have to be moved mechanically and the system requires much space in its functional form.

EP 1 360 935 describes an arrangement of lancets (referred to as "testers") used to obtain liquid samples. The lancets are arranged serially on a tape which has a cover for the lancets on its upper side. A complicated mechanical system is used to expose the lancet for use because the entire lancet body must first be moved out of the plane of the tape in order to be able to use the lancet.

A lancet tape is described in U.S. Publication No. 2004/0193202 in which a part of the lancet body can be bent relative to the tape. A disadvantage associated with this arrangement of tape relative to the lancet is that during a desired lancing movement it is impossible to only move the lancet. Instead, the lancet and tape always have to be moved together. Consequently, a drive mechanism must be selected which is adapted to the tape that includes the lancet. Furthermore, this limitation makes it difficult to achieve a space-saving or uncomplicated design of a simple and light lancing aid.

The prior art devices present a variety of disadvantages. Many mechanical steps are necessary to move the individual lancing element from the magazine store in which the lancets lie in a serial arrangement, i.e., in the plane of the carrier tape, into an arrangement in which the lancet is arranged perpendicular to the plane of the carrier tape. Due to the complicated mechanics, there is an additional disadvantage in that a large amount of space is required for this mechanism. Another disadvantage of many systems of the prior art is the complicated unsealing of the lancet before the lancing operation.

In view of the disadvantages of the prior art, it would be desirable to have a space saving, storable lancing aid that can be used with little mechanical complexity and that enables simple handling.

SUMMARY OF THE INVENTION

The present invention concerns a system for obtaining body fluid which comprises a housing having an opening and contains at least one lancet disposed therein. In its unused (or original) form, the lancet is elongate and substantially straight and has a distal end with a lancet tip (also referred to as a "tip"). In this case, the unused form corresponds to the form of the lancet before it comes into contact for the first time with a guide element. The system additionally comprises a drive unit and a guide element which makes contact with the lancet at least during the lancing operation and thereby guides the movement of the lancet in such a manner that the lancet is bent with reference to the drive direction.

In an exemplary embodiment, the lancet has a high restoring force such that the lancet essentially adopts or returns to its substantially straight form when it is not in contact with the guide element.

The lancet has an elongate extension and one end of which, referred to here as the distal end, is specially shaped for the purpose of insertion into a body, for example, in the form of a tip. In this connection, the tip is a point located at the distal end of the lancet into which the side faces of the elongate lancet body converge. The side faces of the lancet which end at the tip can also have sharp edges. Hence, the lancet consists of at least one lancet body which predominantly has almost parallel side faces or edges and a region at the tip or tip region which directly adjoins the lancet body and has side edges which taper towards one another and end at the tip. The region of the tip, or tip region, can thus be of different sizes depending on the length of the side edges which taper towards one another.

In one embodiment, the lancet is a flat lancet which is bent on its flat side. However, in a different embodiment, a round lancet can be used.

In order to bend the lancet tip, the system has a guide element. This guide element is used to enable the lancet tip to be bent about 5° to 90° relative to the drive direction using the smallest possible application of force. In this connection, the guide element can have various forms. It can, for example, be a single piece or multiple pieces. Its design determines the direction of bending and the extent of bending due to its curved shape. It consists of materials that are suitable for retaining their shape during contact with the lancet in order to adequately guide the lancet. These materials can, for example, be metals, ceramics, glass or plastics. The guide element can be made of a transparent material to enable detection in various wavelength ranges through the guide element.

Furthermore, the guide element can guide the lancet on only one side or completely enclose the lancet as the lancet moves. The guide element can have a closed structure, e.g., in the form of a tube, or an open structure in the form of a channel or rail. The guide element is designed to remain stationary relative to the moving lancet during the process of bending the lancet since the guide element is at least temporarily attached to either the magazine or the housing of the lancing aid. During the bending process, the lancet can be bent over its entire length or only at a section of the lancet such as the tip. The guide element can surround at least a portion of the lancet during the bending process. In doing so, the lancet tip and the sharp edges preferably do not come into direct contact with the guide element so that the tip and sharp edges do not lose their sharpness and therefore become unusable for the lancing operation.

The other portion of the lancet body which adjoins the bending region and merges into the proximal or rear end of the lancet can have a geometry that is different from the tip region such as, for example, a widening or thickening of the lancet body. This broader portion of the lancet body can additionally be made harder in order to have a higher resistance to deformation. This can, for example, be accomplished by the selection of other materials or by suitable choice of the amount or thickness of the materials used. If the lancet is mounted on a carrier, then at least the rear part of the lancet body which preferably has a structure that is more rigid or stiff (and thus resists deformation), can be connected to the carrier in order to make a stable connection with the carrier. The rear part of the lancet body up to the proximal end of the lancet can be used for coupling to a drive unit. For this purpose, the lancet body can have various coupling structures such as grooves, holes, notches or protuberances. The drive movement takes place in alignment with the longitudinal axis of the lancet, whereby the bent lancet tip can be linearly inserted into a body part. In this connection, the opening of the housing is arranged parallel to the drive direction. The orientation of the bent lancet tip, which is different from that of the longitudinal axis of the lancet body, is advantageous in that additional geometric arrangements can be implemented than would be possible with a purely axial drive direction for the lancet body and lancet tip. Furthermore, due to the bending of the lancet tip which, due to its intended use (of being inserted into a body part as painlessly as possible), should be designed to be as thin and fine as possible such that only a small amount of force is necessary or a small material change of the lancet has to be carried out in order to enable an easy bending. This ensures a simple bending of the lancet without increasing the lability of the lancet when it is stored on a carrier or carrier tape. The lancet body, which is used for coupling to the drive unit, can be made stable independent of the design of the tip region in order to withstand both the strain of when the drive unit is coupled and the sustained forces during the lancing movement. It is nevertheless possible to guide the lancet over its complete length through the guide element.

In an embodiment, at least the lancet tip can be provided with a sterile protection which is preferably opened when the lancet is bent.

In one embodiment, the lancet is located on a carrier. The carrier can, for example, be used for the simple storage of a plurality of lancets. In addition, the carrier can also have the function of protecting the lancet against external influences (such as, for example, knocks or other contacts) when the lancet is at least partially surrounded by the carrier. This is particularly useful when the carrier is a carrier tape. In an exemplary embodiment, the lancet body and the lancet tip are attached in an unbent state to the carrier and preferably in a substantially flat position.

A circular structure to which or on which the at least one lancet is fastened can be used alternatively as a carrier. The carrier preferably has a disk-shaped design. However, other carrier structures which, for example, have square, spherical or tape-like, oval or elliptical shapes are conceivable.

In another embodiment, the lancets can also be arranged in a stack magazine in which the lancets are arranged above one another. In this case, the magazine can be part of the system and interact with the system such that it can be exchanged or disposed of. Alternatively, the entire system can be disposable due to the fact that the lancets are stored without an additional magazine. In this case the entire system is discarded after the elements stored in a magazine have been used. In addition to the lancets being elements that can be stored in a magazine, test elements can also be a component of the magazine or the system.

Irrespective of how the storage is carried out, a guide element can be additionally stored for each lancet in an alternative embodiment and the guide element can be moved together with the lancet into a lancing position in the system. In this embodiment, the guide element being disposed in the lancing position, which is located directly under the opening of the housing, can interact with the housing in such a manner that it is locked in position relative to the housing and does not move with the lancet during the lancing operation but instead only guides the lancet.

The lancet and the carrier can be formed in one piece and the lancet can be designed such that it can be bent out of or detached from the carrier. This is preferred when the entire structure is produced from metal such as steel. However, other materials such as ceramics or polymer structures would also allow the lancet and carrier to be formed as one piece.

In an alternative embodiment, the lancet comprises a structure which is suitable for taking up body fluid. This can be a capillary structure, but alternative structures such as hole structures, gap or groove structures are suitable for taking up liquid. In this case a structure formed by stamping in the bend region, preferably in the tip region, can be designed to take up liquid. This embodiment is herein referred to as a microsampler because the sample is taken up by the lancet and not directly by a test element. The structure for taking up body fluid can be preferably located in the tip region. In an alternative embodiment, it can also extend beyond the tip region and extend over parts of the lancet body. The structure for taking up body fluid can be formed in one piece or divided into several regions. In an exemplary embodiment, this structure for taking up liquid begins in the tip region and extends into the lancet body to almost the same extent as in the tip region. In this case the structure for taking up body fluid can open out into the bend region or protrude into the lancet body beyond the bend region. The body fluid collected in the microsampler can be subsequently transferred to a test element and detected by a detection system (e.g., optically or electrochemically) and evaluated by an evaluation system.

In addition, at least one test element can be arranged in, on or next to the carrier or a subsequent carrier. The test element is used to take up the body fluid obtained and to subsequently detect an analyte in the body fluid. The test element can contain reagents for reacting with the analyte. The test element can be attached to a separate carrier or to the carrier of the lancet. In order to prevent contamination of the tip with substances from the test element, the test element is preferably not directly connected to the lancet but is rather arranged on the carrier separate from the lancet. The arrangement of the at least one test element on a separate carrier reduces the risk of contamination. In an exemplary embodiment, a plurality of test elements and a plurality of lancets are arranged relative to one another such that after a tip of an active lancet has been bent, the active lancet and an active test element can be brought into contact by a second movement of the active lancet or of the active test element. This is particularly useful when the active lancet is designed as a microsampler. This can be carried out by a movement of the active lancet relative to the carrier. One method of bringing the active lancet into contact with the active test element is to further bend the active lancet in the first bending direction such that the active lancet tip is bent by more than 90° with reference to the active lancet body. In this embodiment, the active test element is preferably located on a part of the active lancet body. An alternative movement of the active lancet for contacting the active lancet with the active test element is a deflection movement of the active lancet or of the carrier in the opposite direction to that of the first bending movement. In this movement, the tip of the active lancet can be bent back into the plane of the lancet body. As an alternative to contacting the active test element with the active lancet, the body fluid can also be directly transferred from the body part of the user onto the active test element.

Another alternative for contacting the test element with the lancet is to move the test element itself. For this purpose the test element can be located on a second carrier or in a second magazine, in which the carrier of the lancet or of the test element are arranged such that they can at least partly be moved relative to one another.

In one embodiment, the carrier is designed as a carrier tape on which a plurality of lancets are positioned. In this embodiment, a device for obtaining body fluid is described which has an essentially planar carrier tape with a longitudinal and transverse orientation on which at least one lancet comprising a lancet body and tip is arranged, the lancet being arranged substantially horizontally on the carrier tape. The lancet has a sufficiently high restoring force so that in the areas in which it contacts the guide element it can essentially re-adopt or return to its original, substantially straight shape after contact with the guide element. In this connection, the degree to which the lancet is bent before and after contact with the guide element generally does not deviate by more than about 10° from one another. Further, the restoring force and thereby also the stiffness of the lancet depend on various parameters. In one instance, they are determined by the material and its properties, whereby brittle materials are more likely to be unsuitable for being bent. Materials which have a stiffness that is too low such as, for example, thin elastomers or plastic foils are materials which are also less suitable because they do not have an adequate stability for the lancing operation. The lancet should thus be manufactured from a material which has adequate stability so that the lancet is not deformed during the lancing operation, but has an adequate flexibility in order to be bent between about 10° and 90° relative to its unbent form. After force has been exerted by the guide element, the material should return approximately to its original form. This restoring force can be found, for example, in metals and certain polymers and mixtures thereof.

The stiffness should be understood as a measure of the resistance of the material to elastic deformation. This structure should have a lower stiffness than the remaining lancet body so that the lancet can be bent preferably in this region under the action of force. In this process, the orientation of the tip changes relative to the remaining lancet body. This change in orientation is preferably away from the carrier tape plane or lancet body plane. In this process, at least a part of the lancet body remains in its original plane or in the carrier tape plane and can be attached thereto. The force which is required to change the orientation of the lancet tip is also referred to as the threshold force. This threshold force should be of a sufficient magnitude that it changes the orientation of the lancet tip but in so doing, is such that no unintentional deformations occur on the lancet, on the carrier or on the carrier tape.

The transfer of force onto the lancet can take place by means of a guide element which makes contact with the lancet. In the case of lancets which are on a carrier or carrier tape, at least a remainder of the lancet body can remain on the carrier tape during the lancing operation.

In an exemplary embodiment, the guide element comprises two parts. In this embodiment, the lancet tip is driven in a substantially straight path by a push rod during which the lancet is already in contact with the guide element or is thus brought into contact with the guide element during the drive operation. Hence, the lancet can already be present in the guide element either bent or unbent before the lancing operation. In this connection, the guide element can be located at various locations in the system. The lancet can be bent at various locations in the system which results in various arrangements of the drive element and lancet as well as of other components. In this connection, a flat lancet may be advantageous for the arrangement on a carrier or carrier tape.

The material of the lancet is typically metal such as steel. The lancet can, however, also consist of other materials which enable the lancet to be bent when a force acts on it and have sufficient stiffness to be able to penetrate the skin during use without changing shape. Furthermore, the material can be such that the distal end of the lancet can be worked into a sharp tip because otherwise too much pain would be generated during the puncture. The manufacture of lancets is in general sufficiently known in the prior art such as, for example, in DE 19 604 156 or EP 0 565 970.

The carrier tape is preferably produced from a plastic foil. It can, however, also be another more flexible material as described, for example, in U.S. Publication No. 2005/0245845. In an integrated system, at least one test element can be additionally arranged on the carrier tape. The lancet and test element can be provided in an alternating arrangement. The lancet can be attached to the tape diagonally, in a longitudinal orientation as well as in a transverse orientation. One possible embodiment is to arrange the lancet and test element in direct vicinity of one another. This enables direct transfer of liquid onto the test element after the lancing operation without having to move the tape further.

Various methods are herein described for actuating the lancet. The proximal end of the lancet can be attached to the carrier or carrier tape in such a manner that part of the lancet can be moved relative to or with the carrier or carrier tape, whereas the proximal end remains connected to the carrier or carrier tape at one or more points. Another attachment of the lancet is to secure the lancet body on the carrier or carrier tape, whereby the tip region detaches from the carrier or carrier tape. The lancet can be moved in a controlled manner by moving the carrier or carrier tape or by gripping the lancet with a gripper element as a result of which the lancet is moved with or without the carrier or the carrier tape from the plane of the carrier or of the carrier tape. This movement can be executed by means of a drive element which transfers force onto the lancet parallel to the carrier or carrier tape plane. The force is transferred by a drive element which can, for example, be a push rod or a gripper element which grips and moves the body of the lancet. In this connection, the puncture depth of the blood withdrawal device can be freely selected in an embodiment. In order to adjust the puncture depth, the movement of the lancet is defined by a variable stop element against which the lancet impacts during the lancing operation. For this purpose, the body of the lancet can have stop resistances in the form of, for example, thickened portions or wings which can interact with the stop element to stop the movement of the lancet. In this manner the length of the lancet tip which emerges from the housing opening and thus the lancing depth is varied depending on the position of the stop element. The stop element can be integrated into the housing or into the guide element.

The lancet can be driven by ballistic or sliding block-guided mechanisms which are well-known in the art and are described, for example, in DE 19 604 156, EP 0 565 970, U.S. Pat. No. 5,318,584 or U.S. Pat. No. 4,924,879. One embodiment for the lancet drive is the free movement of the lancet after force has been transferred by the drive element such as a push rod. In this embodiment, an impulse is transferred from a drive element onto the lancet and the lancet moves through at least part of the guide element towards the housing opening.

In order to use the system hygienically, the lancet is protected by a sterile protection at least in the tip region. The lancet can be covered by a protective foil over the entire lancet body. The foil can also extend over a part of the carrier tape or carrier and is connected thereto. This sterile protection can consist of a polymer layer which is applied after connecting the lancet to the carrier tape or carrier. The sterile protection can be destroyed or pierced by the lancet tip during the movement of the lancet through the guide element and exposes a portion of the lancet, especially the tip region of the lancet. Alternatively, the sterile protection can be removed before using the lancet. In this case the entire sterile protection is preferably removed.

The invention also concerns a lancing aid for withdrawing body fluid. This lancing aid may consist of a housing having at least one opening and at least one lancet. Conventional lancets (typically flat lancets) and other lancets in which the bending force of the guide element is sufficient to move at least part of the lancet out of the plane of the drive direction can be used in the lancing aid or device. In this process at least part of the lancet emerges from the housing opening and punctures the skin of the patient. As already mentioned, the guide element bends the lancet about 5° to 90° from the drive plane. A drop of blood forms at the puncture site and is used for analysis. If a test element is located in the lancing aid, it can be brought into contact with the drop of blood by transporting the test element below the housing opening. The drop of blood can be applied to the test element without the patient having to initiate further steps. Alternatively, the test element can also be located on a second carrier as already described.

The blood reacts with one or more reagents disposed on the test element such as those that are, for example, known from documents EP 0 885 591, EP 0 535 480 and EP 0 477 322. The test element is analyzed by means of a detector.

The blood can be examined for various components as is known in the art. For example, the analysis can be for blood components such as hematocrit, glucose, cholesterol, coagulation, iron and others. Various methods can be used for the analysis. For example, electrochemical detection reactions can be used, but also optical (e.g. reflection, absorption, fluorescence, Raman-spectroscopy) or magnetic detection reactions. The liquid is typically brought into contact with a test system and a reaction takes place between a test element and the liquid. Thus, detection by means of an optical test element is based on a color reaction between the liquid and detection reagent. Examples of these reactions are described in U.S. Pat. Nos. 3,802,842; 4,061,468 and 4,490,465.

When the instrument is in use the system carries out various steps. If the lancet is already in contact with the guide element, the lancet together with the guide element are brought into a position in which the lancet can be driven by the drive element through the opening of the housing. In this process the sterile protection is preferably destroyed by the lancet. During actuation, at least a portion of the lancet penetrates the skin of the patient and is subsequently retracted into the device. If a microsampler is used, blood can be collected on the lancet in this process. If a transport tape is used, this is transported further and wound onto a spool. In this case, the lancet preferably again lies substantially flat on the carrier tape. This process of restorage in a magazine is described in U.S. Publication No. 2005/0245845.

In an integrated system in which test elements are also attached to the carrier or carrier tape preferably in an alternating arrangement with the lancets, the test element is transported after the lancing operation to the housing opening in order to take up the drop of blood for analysis. The test element can be transported up to the detector and measured there. If a microsampler is used, the collected blood is transferred to a neighboring test element. As already mentioned, the test element can be present on the same carrier or on a second carrier. In this connection, the two carriers can be arranged such that they can be moved relative to one another.

The invention also concerns a lancet which is designed to interact with the guide element such that it is bent during or before the lancing operation. This can be a substantially flat lancet which has sufficient elasticity or restoring force to be able to adopt its original shape without being in contact with the guide element.

The bending of the lancet before or during the lancing operation has various advantages for a system for collecting body fluid. One advantage is the independence of the arrangement of the opening on the housing in relation to the drive direction. In the case of a linear drive of the lancet, the drive element must always be arranged in the same plane relative to the drive direction. This inevitably results in an elongate lancing aid. When it is possible to bend the lancet, the opening on the housing can be positioned at another location so that it is more comfortable to reach for the patient. This can also mean that the device lies more comfortably in the hand and is easier to use.

In addition, other elements such as, for example, test elements or detectors and evaluation units can be easily arranged next to the opening of the housing because the lancet does not permanently block the path to the housing opening. Thus, it is simpler to make the opening accessible to the lancet as well as to the test element. Furthermore, a detection unit can be arranged directly opposite to the opening because neither the lancet nor a drive unit block this opening.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein:

FIG. 2a is a schematic view of a transverse arrangement of lancets on a carrier tape;

FIG. 2b is a schematic view of a longitudinal arrangement of lancets on the carrier tape;

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1A:
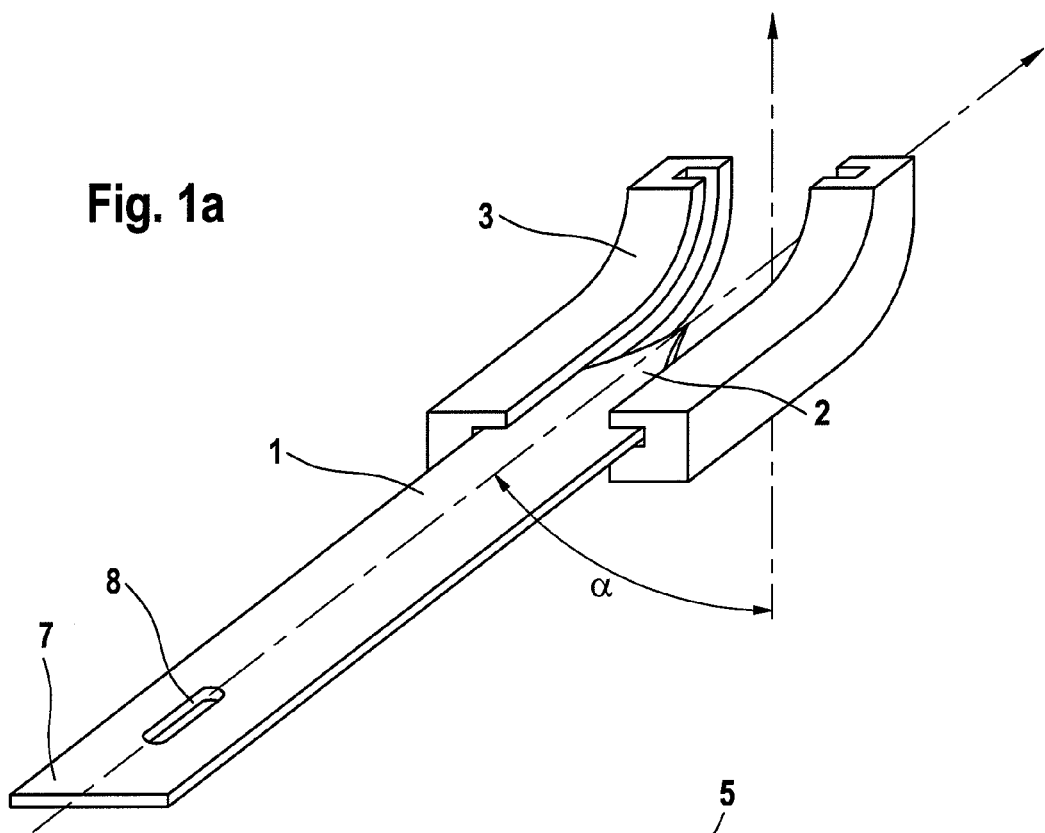
FIG. 1*a* is a schematic view of a lancet interacting with a guide element.

FIG. 1a shows an embodiment of a lancet 1. The lancet 1 has a distal end 2 and a proximal end 7. In FIG. 1a, it is in contact with a guide element 3 which is either located in a magazine of lancets or is connected to the housing of the lancing aid (not shown). The guide element 3 bends the lancet 1 by an angle α, which can be between about 5° and 90° and advantagously between about 40° and 90° from the drive plane before or during the lancing operation. In order to couple a drive unit 4 to the lancet 1, as shown in FIGS. 1b and 1c, the lancet 1 has a coupling device which is in the form of a hole 8.

Figure 1B:
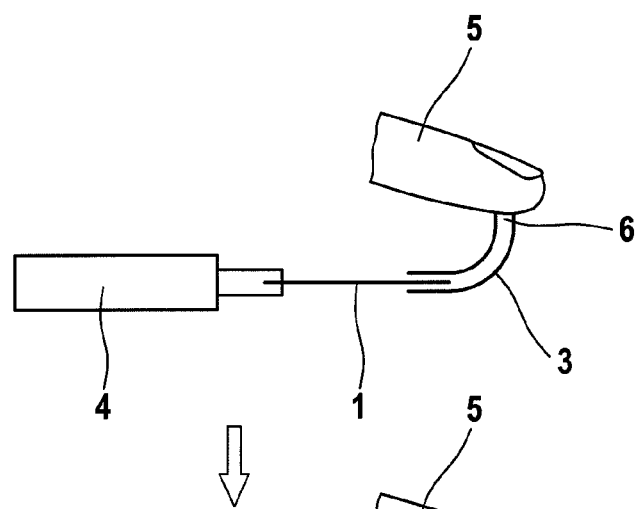
FIG. 1*b* is a schematic view of a lancet before moving in a puncture movement.
Figure 1C:
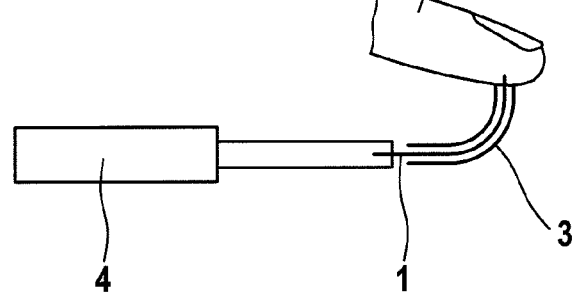
FIG. 1c is a schematic view of a lancet during the puncture movement.

In FIG. 1b, the lancet 1 is shown before the lancing operation with the finger 5 of the patient resting on either the housing or the guide element 3. The lancet 1 is in contact with a drive unit 4, which can move the lancet 1 during a lancing operation. In this case, the lancing site is the opening 6 of the housing (not shown). The opening 6 is positioned on the device by about 90° relative to the drive plane. The lancet is bent to this angle either before or during the lancing operation. This degree of bending can be between about 5° and 90°.

FIG. 2a shows an exemplary arrangement of storing lancets 1 on a carrier tape 14. The lancets 1 are shown after their production. In this embodiment, the lancets 1 are formed out of a thin roll of sheet metal, which in this case represents the carrier tape 14, by punching or etching. The lancet 1 can also be connected at one portion of the lancet, preferably at the proximal end 7, with the carrier tape 14. In this connection, the lancet 1 is attached to the carrier tape 14 in a loose manner such that a substantial portion of the length of the lancet 1 can interact with a guide element 3 (not shown in FIG. 2a). FIG. 2b shows a longitudinal arrangement of lancets on the carrier tape.

In this case, a connecting element can ensure that the lancet is connected to the carrier tape such that the carrier tape does not move during the drive process and there is no interference with the movement of the lancet. This connecting element allows the lancet to be positioned again on the carrier tape after the drive or lancing operation without interacting with other lancets or contaminating them. This connecting element can, for example, consist of an elastic material such as elastomers or other plastics.

Figure 3A:
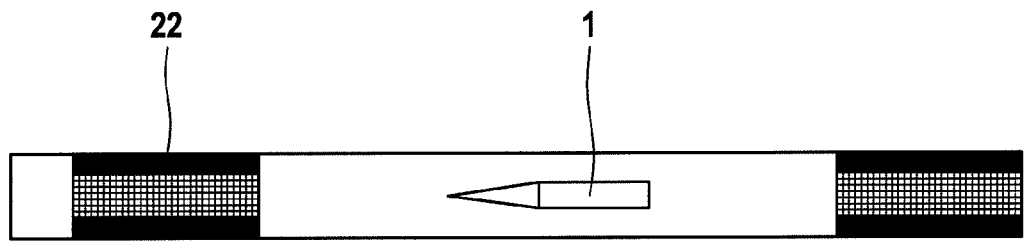
FIG. 3a is a schematic view of the carrier tape with an alternating arrangement of test fields and longitudinally oriented lancets.
Figure 3B:
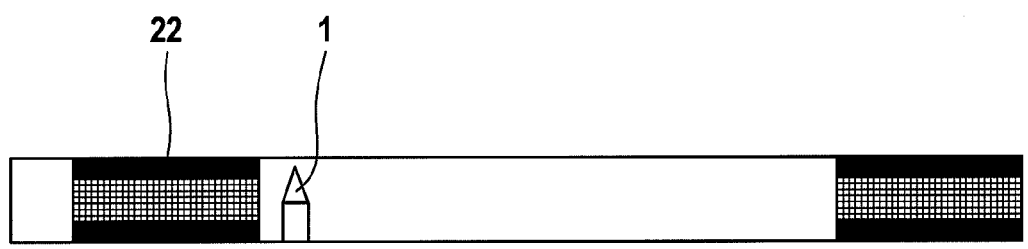
FIG. 3b is a schematic view of the carrier tape with an alternating arrangement of test fields and transversely arranged lancets.

A carrier tape 14 is shown in FIG. 3a on which a test field 22 and a lancet 1 are arranged. The lancet 1 is aligned longitudinally relative to the carrier tape. The distance between the test field 22 and the lancet 1 on the carrier tape 14 can vary. Thus, it is possible that the lancet 1 is placed sufficiently close to the test field 22, such that after the puncture movement, the liquid can be immediately taken up by the test field 22 without moving the carrier tape 14. Another embodiment with test fields 22 and lancets 1 is shown in FIG. 3b. In this embodiment, the lancet 1 is arranged transversely on the carrier tape. Also, the lancet 1 can be placed at a variable distance from the test field 22.

Figure 4:
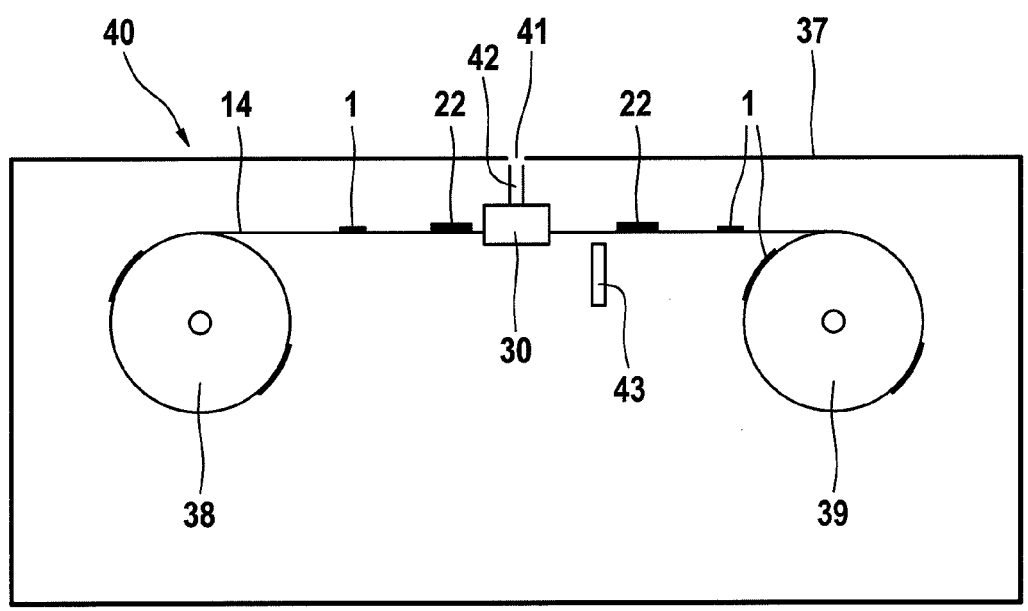
FIG. 4 is a schematic view of an integrated device with a housing and other important components.

An integrated system is shown in FIG. 4. The system comprises a device 40 which includes a housing 37 with an opening 41 and a carrier tape 14 on which lancets 1 are attached. The carrier tape 14 is wound onto two spools 38 and 39. The unused portion of lancets attached to the carrier tape are on spool 38, which is a supply spool, and the used portion are wound onto spool 39, which is a take-up spool. The carrier tape 14 is stretched between the spools 38, 39. The spools 38, 39 are moved by a drive unit such as those known in the art. Preferably, only one of the two spools 38, 39 is driven. An example of such a drive unit is described in U.S. Publication No. 2005/0245845. The lancets 1 are unbent on the carrier tape 14 when the carrier tape 14 is wound onto the spools. A guide element 42, which guides the lancet 1 when it is driven by a drive element 30 and bends the lancet between about 5° and 90° from the drive direction, is located between the two spools 38, 39. In one embodiment, the guide element 42 comprises two separate parts; however, it can also be manufactured as one piece. It can be directly connected to the housing 37 or be a component of the drive element 30. In this embodiment, the drive element 30 and the guide element 42 can be movable within the device so that a detector 43 or other elements of the system can be moved underneath the opening 41.

The guide element 42 can comprise an adjustable element (not shown here) which can change the position of the guide element 42 such that the lancet 1 can protrude from the housing 37 at different distances from the opening 41.

In order to trigger the lancing operation, the carrier tape 14 is wound until an unused lancet 1 is located between the housing opening 41 and drive unit or push rod 30. When the lancing operation is triggered, the push rod 30 moves towards the lancet 1 with so much force that at least the lancet tip 2 is moved out of the housing opening 41. After the puncture, the blood is collected on a test field 22. A reaction between the blood and the reagents on the test field 22 takes effect and which can be analyzed with the aid of the detector 43. The lancet 1 is re-stored together with the carrier tape 14. As a result of its restoring force, the lancet 1 is again integrated substantially flat onto the carrier tape 14.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:
1. A system for withdrawing body fluid, comprising:
    a housing having an opening;
    a flexible lancet having a lancet body and a tip, the lancet being configured substantially straight before use;
    a drive unit for moving the lancet in a drive direction during a lancing operation; and a guide element which contacts and flexes the lancet relative to the drive direction during a movement of the lancet toward the skin for puncture, wherein the guide element is curved.

2. The system of claim 1, wherein the lancet comprises a restoring force which restores the lancet to the substantially straight configuration when the lancet is separated from the guide element.

3. The system of claim 1, wherein the lancet is flexible and substantially flat.

4. The system of claim 1, wherein the guide element comprises metal, ceramic, glass or plastic.

5. The system of claim 1, wherein the lancet is moved through the guide element during the lancing operation.

6. The system of claim 1, wherein the guide element is a rail.

7. The system of claim 6, wherein the rail comprises two rails.

8. The system of claim 1, wherein the guide element bends the lancet to a curved shape during the lancing operation.

9. The system of claim 1, wherein the guide element reorients the tip relative to the drive direction during the lancing operation.

10. The system of claim 1, wherein the guide element reorients the tip between 5° and 90° relative to the drive direction during the lancing operation.

11. The system of claim 1, wherein the guide element reorients the tip about 90° relative to the drive direction during the lancing operation.

12. The system of claim 1, wherein the guide element couples to the housing during the lancing operation.

13. The system of claim 1, wherein, prior to use, the lancet is disposed in a lancet magazine.

14. The system of claim 13, wherein the guide element is connected to the magazine.

15. The system of claim 1, wherein the lancet is arranged on a carrier tape.

16. The system of claim 15, further comprising a test element arranged on the carrier tape.

17. The system of claim 16, wherein the lancet and test element are arranged side by side on the carrier tape.

18. The system of claim 16, wherein, after the bending of the lancet, the lancet contacts the test element to transfer a body fluid sample.

19. The system of claim 15, wherein the lancet is aligned substantially parallel to a longitudinal direction of the carrier tape.

20. The system of claim 15, wherein the lancet is aligned substantially transverse to a longitudinal direction of the carrier tape.

21. The system of claim 15, further comprising a stop element that is integrated into the housing or guide element, wherein, when the tip reaches a maximum puncturing depth, the stop element engages a thickened portion of the lancet body.

22. The system of claim 21, wherein the position of the stop element can be varied to adjust the puncturing depth of the tip.

23. The system of claim 15, further comprising a supply spool and take-up spool.

24. The system of claim 23, wherein, during use, an unused lancet is unwound from the supply spool and is then wound onto the take-up spool after use.

25. The system of claim 24, wherein the lancet comprises a plurality of lancets.

26. The system of claim 1, wherein the lancet comprises a plurality of lancets, and, during the lancing operation, the guide element contacts and bends an active one of the plurality of lancets.

27. The system of claim 26, wherein, after the lancing operation, the active lancet separates from the guide element and returns to an unbent form.

28. The system of claim 26, further comprising a carrier on which the plurality of lancets is arranged.

29. The system of claim 28, wherein the carrier and the plurality of lancets are formed in one piece.

30. The system of claim 28, wherein, prior to use, each of the plurality of lancets comprises an unbent configuration in which each lancet is arranged substantially horizontally on the carrier.

31. The system of claim 30, wherein the tip of the active lancet extends from the carrier when the tip is bent.

32. The system of claim 31, wherein, after the lancing operation, the active lancet returns to the unbent configuration.

33. The system of claim 28, further comprising a plurality of test elements arranged on the carrier.

34. The system of claim 33, wherein the plurality of lancets and the plurality of test elements comprise a side by side arrangement.

35. The system of claim 34, wherein, during the lancing operation, the active lancet makes contact with an active test element after the bending of the active lancet.

36. The system of claim 28, wherein the carrier comprises a carrier tape.

37. The system of claim 28, wherein the carrier is substantially disk shaped.

38. The system of claim 26, further comprising a magazine in which the plurality of lancets is arranged.

39. The system of claim 38, wherein the plurality of lancets is stacked in the magazine.

40. The system of claim 39, wherein the guide element is disposed in the magazine.

41. The system of claim 26, wherein, during the lancing operation, the guide element moves together with the active lancet.

42. The system of claim 1, further comprising a sterile protector that covers the lancet tip before the lancing operation.

43. The system of claim 1, wherein the tip comprises a capillary.

44. The system of claim 1, wherein the lancet comprises a bending region and a rigid region, the bending region being located near the tip and the rigid region being connected to the carrier tape.

45. The system of claim 1, wherein the drive unit and guide element are movable relative to the opening.

46. The system of claim 45, wherein, after the lancing operation and as the drive unit and guide element are moved away from the opening, a detector is moved near the opening to detect a body fluid sample.

47. A device for withdrawing body fluid, comprising:
a housing having an opening;
a substantially planar carrier tape disposed in the housing;
a lancet having a lancet body and tip, the lancet being arranged substantially flat on the carrier tape;

a drive element for driving the lancet in a drive direction during a lancing operation; and a guide element that contacts and bends the lancet during a movement of the lancet toward the skin for puncture such that the lancet tip is reoriented relative to the drive direction, wherein the bending changes the shape of the lancet.

48. The device of claim 47, wherein the lancet returns to the substantially flat arrangement on the carrier tape after use.

49. The device of claim 47, wherein the lancet separates from the guide element and returns to an unbent form after use.

50. The device of claim 47, wherein the reoriented tip is substantially orthogonal to the drive direction.

51. The device of claim 47, wherein the guide element reorients the tip relative to the lancet body.

52. The device of claim 47, wherein the guide element reorients the tip between 5° to 90° relative to the lancet body.

53. The device of claim 47, wherein the guide element reorients the tip about 90° relative to the lancet body.

54. The device of claim 47, wherein the lancet comprises a substantially flat shape.

55. A system for withdrawing body fluid, comprising:
a housing having an opening;
a flexible lancet having a lancet body and a tip, the lancet being configured substantially straight before use;
a drive unit for moving the lancet in a drive direction during a lancing operation; and
a guide element which contacts and flexes the lancet relative to the drive direction during a movement of the lancet toward the skin for puncture, wherein the shape of the guide element determines the flexing direction of the lancet.

56. A system for withdrawing body fluid, comprising:
a housing having an opening;
a flexible lancet having a lancet body and a tip, the lancet being configured substantially straight before use;
a drive unit for moving the lancet in a drive direction during a lancing operation; and
a guide element which contacts and flexes the lancet relative to the drive direction during a movement of the lancet toward the skin for puncture, wherein the lancet moves within the guide element and is flexed by the guide element during the puncture movement.

* * * * *